United States Patent [19]

Takabe et al.

[11] Patent Number: 5,391,537
[45] Date of Patent: Feb. 21, 1995

[54] PICOLINIC ACID DERIVATIVE, AND HERBICIDAL COMPOSITION

[75] Inventors: Fumiaki Takabe, Iwata; Yoshihiro Saito; Masatoshi Tamaru, both of Kakegawa; Shigehiko Tachikawa, Shizuoka; Ryo Hanai, Ogasa, all of Japan

[73] Assignees: Kumiai Chemical Industry Co., Ltd.; Ihara Chemical Industry Co., Ltd., both of Tokyo, Japan

[21] Appl. No.: 960,844

[22] Filed: Oct. 14, 1992

Related U.S. Application Data

[63] Continuation-in-part of Ser. No. 842,163, Mar. 31, 1992, abandoned.

[30] Foreign Application Priority Data

Oct. 25, 1990 [JP] Japan .................. 2-288180

[51] Int. Cl.$^6$ .................. A01N 43/54; C07D 401/12
[52] U.S. Cl. .................. 504/243; 504/242; 504/239; 504/193; 544/300; 544/310; 544/316; 544/320; 544/321; 544/331; 544/229; 544/296
[58] Field of Search .......... 544/300, 310, 316, 320, 544/321, 331, 229, 296; 504/239, 242, 243, 193

[56] References Cited

U.S. PATENT DOCUMENTS

| | | | |
|---|---|---|---|
| 5,015,285 | 5/1991 | Rheinheimer | 544/300 |
| 5,085,685 | 2/1992 | Rheinheimer | 504/242 |
| 5,125,957 | 6/1992 | Hiratsuka et al. | 544/301 |

FOREIGN PATENT DOCUMENTS

| | | |
|---|---|---|
| 64-84 | 1/1989 | Japan . |
| 1-213202 | 8/1989 | Japan . |
| 2-121973 | 5/1990 | Japan . |
| 2-216631 | 8/1990 | Japan . |
| 3-106876 | 5/1991 | Japan . |

Primary Examiner—John M. Ford
Attorney, Agent, or Firm—Oblon, Spivak, McClelland, Maier & Neustadt

[57] ABSTRACT

The present invention is to provide a novel picolinic acid derivative having the formula,

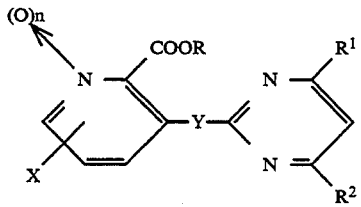

(wherein R is a hydrogen atom, an alkyl group or others, $R^1$ and $R^2$ are the same or different, and are an alkyl group, an alkoxy group or others, X is a cyano group, a phenoxy group or others, Y is an oxygen atom or others, and n is 0 or 1) or a salt thereof; a method for preparing the same; and a herbicidal composition containing the same as an active ingredient.

The picolinic acid derivative or the salt thereof of the present invention achieves an excellent herbicidal effect at a low dosage, and is effective for controlling the growth of various weeds in a wide range.

The picolinic acid derivative or the salt thereof of the present invention can be applied to a paddy field, a cultivated field, a non-agricultural land and the like as a herbicidal composition.

13 Claims, No Drawings

PICOLINIC ACID DERIVATIVE, AND HERBICIDAL COMPOSITION

This application is a continuation-in-part application of Ser. No. 07/842,163, filed Mar. 31, 1992, now abandoned, which application is the U.S. National Phase application corresponding to PCT/JP91/01459, filed Oct. 25, 1991.

BACKGROUND OF THE INVENTION

1. Field of the Invention

The present invention relates to a novel picolinic acid derivative useful as a herbicidal composition, and a herbicidal composition containing the same which is applicable to a paddy field, a cultivated field and a non-agricultural land.

2. Dicussion of Background

Heretofore, as a picolinic acid derivative having a herbicidal activity, there were known ethyl 3-(4,6-dimethoxypyrimidin-2-yl)oxypicolinate (see for example, Japanese Unexamined Patent Publication No. 84/1989 and EP-249707) and methyl 3-(4,6-dimethoxypyrimidin-2yl)thiopicolinate (see for example, Japanese Unexamined Patent Publication No. 121973/1990 and EP-360163).

SUMMARY OF THE INVENTION

In recent years, a number of herbicides have been developed and practically used, and they have contributed to the saving of energy for the agricultural operations and to the improvement of the production efficiency. However, in their practical use, such herbicides have various problems with respect to the herbicidal effects and the safety to crop plants. For example, weeds such as barnyardgrass (*Echinochola crusgalli*), morningglory (Ipomuea spp), common cocklebur (*Xanthum strumarium*), quackgrass (*Agropyron repens*), johnsongrass (*Sorghum halepense*), etc. are distributed widely throughout the world, and it is very difficult to control them. Various herbicides have been used to control these weeds, but none of them are fully satisfactory with respect to the certainty of the herbicidal effects and the safety to crop plants. Therefore, it has been desired to develop an improved herbicide.

The present inventors have conducted extensive research on picolinic acid derivatives with an aim to solve the above-mentioned problems, and as a result, have found that the compound of the present invention having substituents such as dialkylamino, monoalkylamino or amino group introduced into the pyridine rings of pyrimidinyloxypicolinic acid derivatives, exhibits excellent herbicidal effects providing a wide herbicidal spectrum against annual, perennial, gramineous and broadleaf weeds at a very small dose. The present invention has been accomplished on the basis of these discoveries.

Thus, the picolinic acid derivative of the present invention has the formula:

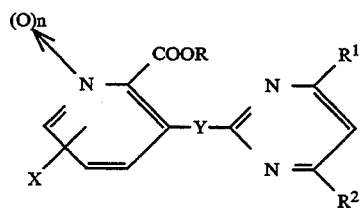

(wherein R is a hydrogen atom, an alkyl ($C_1$–$C_4$) group, an alkenyl ($C_2$–$C_4$) group, an alkynyl ($C_2$–$C_4$) group, a benzyl group, a halogen-substituted alkyl ($C_1$–$C_4$) group, a cyanoalkyl ($C_1$–$C_4$) group, an alkoxy ($C_1$–$C_4$) alkyl ($C_1$–$C_4$) group, an alkoxy ($C_1$–$C_4$) carbonyloxyalkyl ($C_1$–$C_4$) group, an alkoxy ($C_1$–$C_4$) carbonylalkyl ($C_1$–$C_4$) group, an alkylcarbonyl ($C_2$–$C_7$) oxyalkyl ($C_1$–$C_4$) group, a cycloalkylcarbonyl ($C_4$–$C_7$) oxyalkyl ($C_1$–$C_4$) group, a cycloalkyl ($C_3$–$C_6$) alkyl ($C_1$–$C_4$) group, an alkali metal atom such as sodium and potassium, an alkali earth metal atom such as calcium, or, an organic amine cation such as a lower alkylamine and a di-lower alkyl amine; $R^1$ and $R^2$ are the same or different, and are a lower alkyl group, a lower alkoxy group, a halogen-substituted lower alkoxy group, an alkylsulfonyl ($C_1$–$C_4$) group, or a halogen atom;

X is a group having the formula

(wherein $R^3$ and $R^4$ are the same or different, and are a hydrogen atom, a lower alkyl group, a phenyl group or an acyl group), a cyano group, a phenyl group (which may be substituted with a halogen atom, a lower alkyl group or a lower alkoxy group), a phenoxy group, a halogen-substituted alkyl ($C_1$–$C_4$) group, an alkoxy ($C_1$–$C_4$) group, an alkenyl ($C_2$–$C_4$) group, an alkynyl ($C_2$–$C_4$) group, a hydroxyl group, a nitro group, a trimethylsilylethynyl group, a 4,6-dimethoxypyrimidin-2-yloxy group or a hydrogen atom; Y is an oxygen atom or a group having the formula

(wherein $R^5$ is a hydrogen atom or a formyl group); and n is 0 or 1;

provided that when X is a hydrogen atom, Y is a group having the formula,

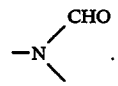

Examples of the lower alkyl group used herein include methyl, ethyl, propyl, butyl and the like; examples of the lower alkoxy group include methoxy, ethoxy, propoxy, butoxy and the like; examples of the cycloalkyl group include cyclopropyl, cyclopentyl, cyclohexyl and the like; examples of the acyl group include a formyl group and an alkylcarbonyl group; examples of the alkylcarbonyl group include acetyl, propionyl, butyryl, valeryl, pivaloyl, hexanoyl and the like; and examples of the halogen atom include chlorine, bromine, fluorine and the like.

Examples of the salt of the picolinic acid derivative include chloride, sulfate, oxalate and the like.

Now, specific examples of the compound of the present invention will be presented in Table 1. Compound numbers given in the Table will be referred to in the subsequent description in the specification.

TABLE 1

[Structure: pyridine with COOR at 2-position, N in ring, X substituent; connected via Y to pyrimidine with R¹ and R² substituents]

| Compound No. | X | Y | R | R¹ | R² | Physical properties Melting point (°C.) |
|---|---|---|---|---|---|---|
| 1 | 6-OCH₃ | O | CH₃ | OCH₃ | OCH₃ | 148–150 |
| 2 | 6-OCH₃ | O | H | OCH₃ | OCH₃ | 137–139 |
| 3 | 6-OC₂H₅ | O | CH₃ | OCH₃ | OCH₃ | 112–113 |
| 4 | 6-OC₂H₅ | O | H | OCH₃ | OCH₃ | 138–139 |
| 5 | 6-OH | O | CH₃ | OCH₃ | OCH₃ | 186–190 |
| 6 | 6-O-(4,6-dimethoxypyrimidin-2-yl) | O | CH₃ | OCH₃ | OCH₃ | 131–132 |
| 7 | 6-O-(4,6-dimethoxypyrimidin-2-yl) | O | H | OCH₃ | OCH₃ | 189–192 |
| 8 | 6-phenyl | O | CH₃ | OCH₃ | OCH₃ | 92–94 |
| 9 | 6-(4-fluorophenyl) | O | CH₃ | OCH₃ | OCH₃ | 110–113 |
| 10 | 6-(4-fluorophenyl) | O | H | OCH₃ | OCH₃ | 159–163 |
| 11 | 6-(4-chlorophenyl) | O | CH₃ | OCH₃ | OCH₃ | 146.5–149 |
| 12 | 6-(4-chlorophenyl) | O | H | OCH₃ | OCH₃ | 167–170 |
| 13 | 6-(4-methylphenyl) | O | CH₃ | OCH₃ | OCH₃ | 113–116 |
| 14 | 6-(4-methylphenyl) | O | H | OCH₃ | OCH₃ | 155–158 |
| 15 | 6-(4-methoxyphenyl) | O | CH₃ | OCH₃ | OCH₃ | 111–114 |

TABLE 1-continued

[Structure: pyridine ring with COOR at 2-position, N in ring, X at 6-position, Y-C(=N)(N) linkage to pyrimidine bearing R¹ and R² substituents]

| Compound No. | X | Y | R | R¹ | R² | Physical properties Melting point (°C.) |
|---|---|---|---|---|---|---|
| 16 | 6-(p-OCH₃-phenyl) | O | H | OCH₃ | OCH₃ | 168–172 |
| 17 | 6-NO₂ | O | CH₃ | OCH₃ | OCH₃ | |
| 18 | 6-O-phenyl | O | CH₃ | OCH₃ | OCH₃ | |
| 19 | 6-N(CH₃)₂ | O | CH₃ | OCH₃ | OCH₃ | 125–127 |
| 20 | 6-N(CH₃)₂ | O | H | OCH₃ | OCH₃ | 195–197.5 |
| 21 | 6-N(CH₃)₂ | O | CH₃ | OCH₃ | CH₃ | 106–108 |
| 22 | 6-N(CH₃)₂ | O | CH₃ | Cl | OCH₃ | 120–122 |
| 23 | 6-N(CH₃)₂ | O | CH₃ | Cl | CH₃ | 154–158 |
| 24 | 6-N(CH₃)₂ | O | CH₃ | OCHF₂ | OCH₃ | 67–69 |
| 25 | 6-CN | O | CH₃ | OCH₃ | OCH₃ | 132–136 |
| 26 | 6-NH₂ | O | CH₃ | OCH₃ | OCH₃ | 67–69 |
| 27 | 6-N(C₂H₅)₂ | O | CH₃ | OCH₃ | OCH₃ | 109–112 |
| 28 | 6-NH-phenyl | O | CH₃ | OCH₃ | OCH₃ | |
| 29 | 6-NHCOCH₃ | O | CH₃ | OCH₃ | OCH₃ | 80–85 |
| 30 | 6-NHCO-phenyl | O | CH₃ | OCH₃ | OCH₃ | |
| 31 | 6-H | NCHO | CH₃ | OCH₃ | OCH₃ | |
| 32 | 6-N(CH₃)₂ | NCHO | CH₃ | OCH₃ | OCH₃ | |
| 33 | 6-N(CH₃)₂ | O | CH₃ | CH₃ | SO₂CH₃ | 150–152.5 |
| 34 | [N-oxide pyridine structure: 6-N(CH₃)₂, 2-COOCH₃, 3-O-linked pyrimidine with OCH₃, OCH₃] | | | | | 132–134 |
| 35 | 6-N(CH₃)₂ | O | C₂H₅ | OCH₃ | OCH₃ | 112–113 |
| 36 | 6-N(CH₃)₂ | O | C₃H₇ | OCH₃ | OCH₃ | 83.5–85 |
| 37 | 6-N(CH₃)₂ | O | C₃H₇-i | OCH₃ | OCH₃ | 62–68 |
| 38 | 6-N(CH₃)₂ | O | CH₃COOC₂H₅ | OCH₃ | OCH₃ | 113–115 |
| 39 | 6-N(CH₃)₂ | O | CH(CH₃)OCOC₂H₅ | OCH₃ | OCH₃ | Not measurable |
| 40 | 6-N(CH₃)₂ | O | CH(CH₃)OCOOC₂H₅ | OCH₃ | OCH₃ | 1.5215 |
| 41 | 6-N(CH₃)₂ | O | CH₂OCH₃ | OCH₃ | OCH₃ | 91–96 |
| 42 | 6-N(CH₃)₂ | O | CH₂CN | OCH₃ | OCH₃ | 143–145.5 |
| 43 | 6-N(CH₃)₂ | O | CH₂CH₂Cl | OCH₃ | OCH₃ | 94–97 |
| 44 | 6-N(CH₃)₂ | O | CH₂C≡CH | OCH₃ | OCH₃ | 127–130 |
| 45 | 6-N(CH₃)₂ | O | CH₂CH=CH₂ | OCH₃ | OCH₃ | 92–94 |

TABLE 1-continued

Structure: pyridine with COOR at position 2, Y-linked pyrimidine (with R¹, R²) at position 3, X at position 6.

| Compound No. | X | Y | R | R¹ | R² | Physical properties Melting point (°C.) |
|---|---|---|---|---|---|---|
| 46 | 6-N(CH$_3$)$_2$ | O | CH$_2$–C$_6$H$_5$ (benzyl) | OCH$_3$ | OCH$_3$ | 126–130 |
| 47 | 6-N(CH$_3$)$_2$ | O | Na$^\oplus$ | OCH$_3$ | OCH$_3$ | 148–157 |
| 48 | 6-N(CH$_3$)$_2$ | O | K$^\oplus$ | OCH$_3$ | OCH$_3$ | 240–245 |
| 49 | 6-N(CH$_3$)$_2$ | O | ½Ca$^{\oplus\oplus}$ | OCH$_3$ | OCH$_3$ | 169–182 |
| 50 | 6-N(CH$_3$)$_2$ | O | CH(CH$_3$)OCOC$_3$H$_7$ | OCH$_3$ | OCH$_3$ | 46–48 |
| 51 | 6-N(CH$_3$)$_2$ | O | CH(CH$_3$)OCOC$_4$H$_9$ | OCH$_3$ | OCH$_3$ | 59–60 |
| 52 | 6-N(CH$_3$)$_2$ | O | CH(CH$_3$)OCOC$_5$H$_{11}$ | OCH$_3$ | OCH$_3$ | 63–64.5 |
| 53 | 6-N(CH$_3$)$_2$ | O | CH$_2$OCOC(CH$_3$)$_3$ | OCH$_3$ | OCH$_3$ | 113.5–115 |
| 54 | 6-N(CH$_3$)$_2$ | O | CH$_2$OCO–cyclopentyl | OCH$_3$ | OCH$_3$ | 101–102 |
| 55 | 6-N(CH$_3$)$_2$ | O | CH$_2$–cyclopropyl | OCH$_3$ | OCH$_3$ | 65–67 |
| 56 | 6-CH=CH$_2$ | O | CH$_3$ | OCH$_3$ | OCH$_3$ | 65–67 |
| 57 | 6-CH=CH$_2$ | O | H | OCH$_3$ | OCH$_3$ | 106–107 |
| 58 | 6-C≡CH | O | CH$_3$ | OCH$_3$ | OCH$_3$ | |
| 59 | 6-C≡CH | O | H | OCH$_3$ | OCH$_3$ | |
| 60 | 6-CF$_3$ | O | CH$_3$ | OCH$_3$ | OCH$_3$ | |
| 61 | 6-CF$_3$ | O | H | OCH$_3$ | OCH$_3$ | |
| 62 | 6-C≡C–Si(CH$_3$)$_3$ | O | CH$_3$ | OCH$_3$ | OCH$_3$ | 95–97 |
| 63 | (6-N(CH$_3$)$_2$ pyridine, COOH, Y=O, pyrimidine with OCH$_3$, OCH$_3$)·HCl | | | | | 188–189 |
| 64 | 6-N(CH$_3$)$_2$ | O | NH(C$_3$H$_7$-i)$_2$ | OCH$_3$ | OCH$_3$ | |
| 65 | 6-N(CH$_3$)$_2$ | NH | H | OCH$_3$ | OCH$_3$ | |
| 66 | 6-NHCH$_3$ | O | CH$_3$ | OCH$_3$ | OCH$_3$ | 137–138 |
| 67 | 6-NHCH$_3$ | O | H | OCH$_3$ | OCH$_3$ | 160–162 |
| 68 | 6-NHCH$_3$ | O | Na$^\oplus$ | OCH$_3$ | OCH$_3$ | |
| 69 | 6-NHCH$_3$ | O | K$^\oplus$ | OCH$_3$ | OCH$_3$ | |
| 70 | 6-NHCH$_3$ | O | ½Ca$^{\oplus\oplus}$ | OCH$_3$ | OCH$_3$ | |
| 71 | 6-NHCH$_3$ | O | C$_3$H$_7$-i | OCH$_3$ | OCH$_3$ | |
| 72 | 6-NHCH$_3$ | O | CH$_2$OCH$_3$ | OCH$_3$ | OCH$_3$ | |
| 73 | 6-NHCH$_3$ | O | CH(CH$_3$)OCOC$_4$H$_9$ | OCH$_3$ | OCH$_3$ | |

TABLE 1-continued

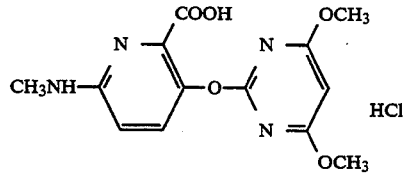

| Compound No. | X | Y | R | R¹ | R² | Physical properties Melting point (°C.) |
|---|---|---|---|---|---|---|
| 74 | 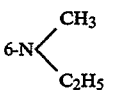 | | | | | |
| 75 | 6-N(CH₃)(C₂H₅) | O | CH₃ | OCH₃ | OCH₃ | 94–97 |
| 76 | 6-N(CH₃)(C₂H₅) | O | H | OCH₃ | OCH₃ | 168–170 |
| 77 | 6-N(CH₃)(C₃H₇) | O | CH₃ | OCH₃ | OCH₃ | 86–87 |
| 78 | 6-N(CH₃)(C₃H₇) | O | H | OCH₃ | OCH₃ | 99–100 |
| 79 | 6-N(CH₃)(C₄H₉) | O | CH₃ | OCH₃ | OCH₃ | 88–90 |
| 80 | 6-N(CH₃)(C₄H₉) | O | H | OCH₃ | OCH₃ | 105–107 |
| 81 | 6-N(C₂H₅)₂ | O | H | OCH₃ | OCH₃ | 159–161 |
| 82 | 6-N(C₃H₇)₂ | O | CH₃ | OCH₃ | OCH₃ | |
| 83 | 6-N(C₃H₇)₂ | O | H | OCH₃ | OCH₃ | 140–143 |
| 84 | 6-N(C₃H₇-i)₂ | O | CH₃ | OCH₃ | OCH₃ | Not measurable |
| 85 | 6-N(C₃H₇-i)₂ | O | H | OCH₃ | OCH₃ | 131–132 |
| 86 | 6-NH₂ | O | H | OCH₃ | OCH₃ | 235–237 |
| 87 | 6-NHC₂H₅ | O | CH₃ | OCH₃ | OCH₃ | 75–96 |
| 88 | 6-NHC₂H₅ | O | H | OCH₃ | OCH₃ | 170–171 |
| 89 | 6-NHC₃H₇ | O | CH₃ | OCH₃ | OCH₃ | 114–115 |
| 90 | 6-NHC₃H₇ | O | H | OCH₃ | OCH₃ | 182–183 |
| 91 | 6-NHC₃H₇-i | O | CH₃ | OCH₃ | OCH₃ | 116–119 |
| 92 | 6-NHC₃H₇-i | O | H | OCH₃ | OCH₃ | 177–181 |
| 93 | 6-(C₃)₂N | O | CH₂OCOC₄H₉-s | OCH₃ | OCH₃ | 89–90 |
| 94 | 6-H₂N | O | C₂H₅ | OCH₃ | OCH₃ | |
| 95 | 6-C₄H₉NH | O | CH₃ | OCH₃ | OCH₃ | 67–68 |
| 96 | 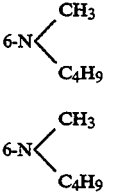 | | | | | 168–169 |
| 97 | 6-CH₂N(C₂H₅) | O | C₃H₇-i | OCH₃ | OCH₃ | 1.5482 |
| 98 | 6-CH₂N(C₃H₉) | O | CH₂CO₂CH₃ | OCH₃ | OCH₃ | 1.5421 |
| 99 | 6-s-C₄H₉NH | O | CH₃ | OCH₃ | OCH₃ | |
| 100 | 6-s-C₄H₉NH | O | H | OCH₃ | OCH₃ | |

TABLE 1-continued

[structure diagram with COOR, R¹, R², X, Y]

| Compound No. | X | Y | R | R¹ | R² | Physical properties Melting point (°C.) |
|---|---|---|---|---|---|---|
| 101 | 6-i-C3H9N(CH3) | O | CH3 | OCH3 | OCH3 | 111–113.5 |
| 102 | 6-i-C3H9N(CH3) | O | H | OCH3 | OCH3 | 59.5–64 |
| 103 | 6-i-C4H9N(CH3) | O | CH3 | OCH3 | OCH3 | 91–92.5 |
| 104 | 6-i-C4H9N(CH3) | O | H | OCH3 | OCH3 | 84–86 |
| 105 | 6-s-C4H9N(CH3) | O | CH3 | OCH3 | OCH3 | 66–70 |
| 106 | 6-s-C4H9N(CH3) | O | H | OCH3 | OCH3 | 106–108 |
| 107 | 6-(CH3)2N | O | H | Cl | CH3 | 154–155 |
| 108 | [structure with (CH3)2N—, +N—CH3, COOCH3, OCH3, OCH3, .I⁻] | | | | | 168–169 |

*In Table 1, the physical property of Compound Nos. 40, 97 and 98 are indicated by refractive index (by sodium-D ray at 20° C.).

Examples of a process for preparing the compound of the present invention are illustrated hereinafter, but the production method is not restricted to such processes.

<Process A>

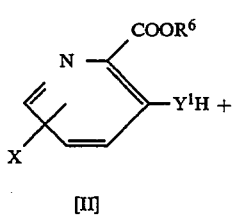

[II]

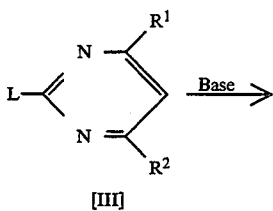

[III]

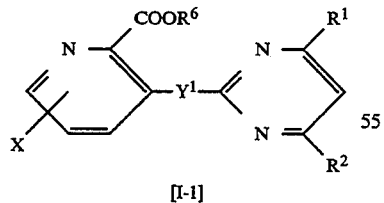

[I-1]

(wherein R¹ R² and X are as defined above; R⁶ is R other than a hydrogen atom; L is a halogen atom, an alkylsulfonyl group or a benzylsulfonyl group; and Y¹ is an oxygen atom, or a group having the formula —N<-CHO.)

The compound of the formula I-1 of the present invention can be produced by reacting the compound of the formula II with a pyrimidine derivative of the formula III in the presence of a base, preferably in an inert solvent, within a temperature range of from room temperature to the boiling point of the solvent for from a few minutes to a few hours.

Here, examples of the solvent used include a hydrocarbon solvent such as benzene or toluene, a halogenated hydrocarbon solvent such as dichloromethane or chloroform, an ether solvent such as tetrahydrofuran or 1,4-dioxane, a ketone solvent such as acetone or methyl ethyl ketone, an ester solvent such as methyl acetate or ethyl acetate, an aprotic polar solvent such as dimethylformamide or dimethylacetamide, or acetonitrile. Examples of the base used include an alkali metal such as metal sodium or metal potassium, an alkali metal hydride or alkali earth metal hydride such as sodium hydride, potassium hydride or calcium hydride, a carbonate such as sodium carbonate, potassium carbonate or calcium carbonate, or a metal hydroxide such as sodium hydroxide, potassium hydroxide or calcium hydroxide.

A compound wherein Y is —NH—, can be prepared by applying an acid or a base to a compound wherein Y is

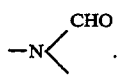

<Process B>

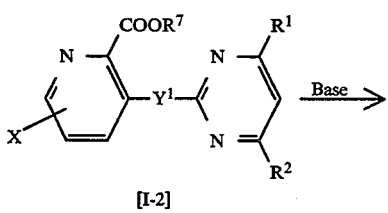

[I-2]

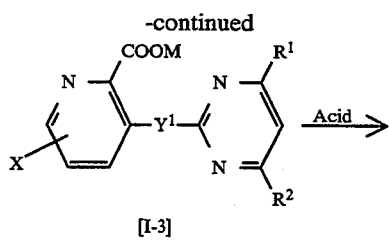

[I-3]

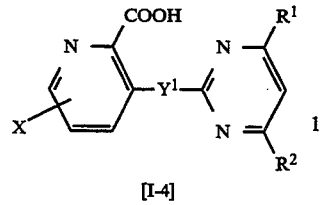

[I-4]

(wherein $R^1$, $R^2$, X and $Y^1$ are as defined above; M is an alkali metal or an alkali earth metal; and $R^7$ is an ester-forming group of R.)

Thus, the compound of the formula I-3 can be prepared by reacting in the presence of a base in a solvent such as a polar solvent, water or a mixture of water and a polar solvent within a temperature range of from room temperature to the boiling point of the solvent for from several hours to several tens hours.

The product thus prepared is then precipitated with an aqueous solution of an organic acid such as citric acid and acetic acid or a mineral acid such as hydrochloric acid and sulfuric acid to obtain the compound of the formula I-4.

Examples of the solvent used include an alcohol solvent such as methanol and ethanol, an ether polar solvent such as 1,4-dioxane and tetrahydrofuran, and an amide polar solvent such as dimethylformamide and dimethylacetamide, but are not limited thereto. Examples of the base used include carbonates such as sodium carbonate, potassium carbonate and calcium carbonate, and metal hydroxides such as sodium hydroxide, potassium hydroxide and calcium hydroxide.

<Process C>

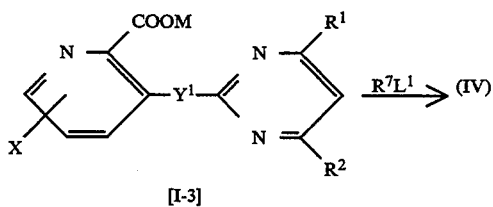

(wherein $R^1$, $R^2$, $R^7$, M, X and $Y^1$ are as defined above, and $L^1$ is a halogen atom.)

The compound of the formula I-5 can be prepared by reacting the compound of the formula I-3 with the compound of the formula IV in a polar solvent, preferably an inert solvent, within a temperature range of from room temperature to the boiling point of the solvent for from a few minutes to a few hours.

Examples of the solvent used include a hydrocarbon solvent such as benzene or toluene, a halogenated hydrocarbon solvent such as dichloromethane or chloroform, an ether solvent such as 1,4-dioxane or tetrahydrofuran, a ketone solvent such as acetone or methyl ethyl ketone, an ester solvent such as methyl acetate or ethyl acetate, an amide type aprotic polar solvent such as dimethylformamide or dimethylacetamide, and acetonitrile.

<Process D>

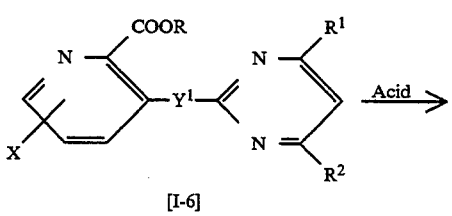

[I-6]

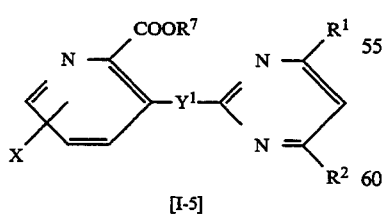

[I-7]

(wherein R, $R^1$, $R^2$, X and Y1 are as defined above.)

The compound of the formula I-7 can be prepared by reacting the compound of the formula I-6 with an acid in an inert solvent within a temperature range of from room temperature to the boiling point of the solvent for from a few minutes to a few hours.

Examples of the solvent used include a hydrocarbon solvent such as benzene or toluene, a halogenated hydrocarbon solvent such as dichloromethane or chloroform, an ether solvent such as 1,4-dioxane or tetrahydrofuran, a ketone solvent such as acetone or methyl ethyl ketone, an ester solvent such as methyl acetate or ethyl acetate, an aprotic polar solvent such as dimethylformamide or dimethylacetamide, and acetonitrile. Examples of an acid used include hydrochloric acid, sulfuric acid and oxalic acid. The acid may be directly added to the inert solvent, or it may be added in the form of gas.

<Process E>

[I-8]

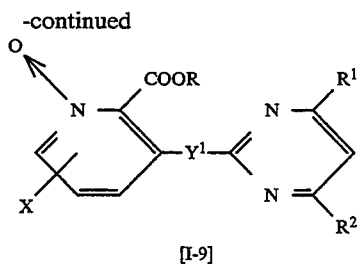

[I-9]

(wherein $R^1$, $R^2$, X and $Y^1$ are as defined above.)

The compound of the formula I-9 can be prepared by reacting the compound of the formula I-8 with a peroxide in an inert solvent within a temperature range of from −20° C. to the boiling point of the solvent.

Examples of the solvent used include, preferably, methanol, water, dichloromethane and chloroform. Examples of the peroxide used include hydrogen peroxide or organic peroxide such as methachloroperbenzoic acid and benzoyl peroxide.

Best Mode for Carrying out the Invention obtain the present invention will be described in further detail with reference to Examples.

EXAMPLE 1

Preparation of methyl 3-(4,6-dimethoxypyrimidin-2-yl)oxy-6-(N,N-dimethylamino)picolinate (Compound No. 19)

1.4 g (7 mmol) of methyl 6-(N,N-dimethylamino)-3-hydroxypicolinate, 1.6 g (7 mmol) of 4,6-dimethoxy-2-methylsulfonylpyrimidine and 0.6 g (4 mmol) of potassium carbonate were added to 100 ml of dimethylformamide (DMF), and were reacted at 90° C. for 2 hours. After the reaction, the reaction content was poured into water, and was extracted with diethyl ether, and then washed with water, dried and concentrated to obtain an oily product which was thereafter crystallized with isopropyl ether. The crystal thus obtained was recrystallized with ethyl acetate/n-hexane to obtain an aimed product.

Yield: 1.6 g (66%), Melting point: 125°–127° C.

EXAMPLE 2

Preparation of methyl 3-(4,6-dimethoxypyrimidin-2-yl)oxy-6-phenylpicolinate (Compound No. 8)

1.0 g (4.4 mmol) of methyl 6-phenyl-3-hydroxypicolinate, 0.8 g (4 mmol) of 4,6-dimethoxy-2-methylsulfonylpyrimidine and 0.6 g (4 mmol) of potassium carbonate were added to 20 ml of DMF, and were reacted at 80° C. for 0.5 hour. After the reaction, the reaction content was poured into water, and was extracted with ethyl acetate. The organic layer thus obtained was washed with water and a saturated salt water, dried and treated with an appropriate amount of Florisil. Ethyl acetate was then distilled off under reduced pressure, and the residue was crystallized by adding 20 ml of hexane thereto and allowing to stand for 3 days. The crystal thus obtained was washed with hexane/isopropyl ether to obtain an aimed compound.

Yield: 0.85 g (58%), Melting point: 92°–94° C.

EXAMPLE 3

Preparation of 3-(4,6-dimethoxypyrimidin-2-yl)oxy-6-(N,N-dimethylamino)picolinic acid (Compound No. 20)

2.5 g (7.7 mmol) of methyl 3-(4,6-dimethoxypyrimidin-2-yl)oxy-6-(N,N-dimethylamino) picolinate was dissolved in 100 ml of methanol, and 6 ml of 10% potassium hydroxide aqueous solution was mixed therewith. The resultant mixture was stirred at room temperature for one night. After the reaction, the reaction content was poured into water, and was extracted with ethyl acetate. The aqueous layer was made acidic, and was extracted with chloroform, and then washed with water, dried and concentrated to obtain a crystal which was then washed with isopropyl ether to obtain an aimed compound.

Yield: 1.6 g (64%), Melting point: 195°–197.5° C.

EXAMPLE 4

Preparation of 1-(ethoxycarbonyloxy)ethyl 3-(4,6-dimethoxypyrimidin-2-yl)oxy-6-dimethylaminopicolinate (Compound No. 40)

2.0 g (5.6 mmol) of potassium 3-(4,6-dimethoxypyrimidin-2-yl)oxy-6-dimethylaminopicolinate and 0.8 g (5.7 mmol) of 1-(ethoxycarbonyloxy) ethylchloride were suspended in 5 ml of dimethylformamide, and were stirred at room temperature for 6 hours. The reaction mixture was poured into water, and was extracted with ethyl acetate twice. The organic layer was then washed with water and dried, and the solvent was distilled off to obtain a viscous product which was then column-purified to obtain an aimed compound.

Yield: 0.5 g (33%), Refractive index (Na-D ray): 1.5215

EXAMPLE 5

Preparation of potassium 3-(4,6-dimethoxypyrimidin-2-yl)oxy-6-dimethylaminopicolinate (Compound No. 48)

9.2 g (27.5 mmol) of methyl 3-(4,6-dimethoxypyrimidin-2-yl)oxy-6-dimethylaminopicolinate was dissolved in 30 ml of methanol, and 1.55 g (27.5 mmol) of 10% potassium hydroxide was added thereto. Furthermore, 20 ml of water was added thereto, and the resultant mixture was stirred at room temperature. The reaction liquor was concentrated under reduced pressure, and acetone was added thereto to precipitate a crystal. The crystal thus obtained was separated by filtration and was washed with hexane to obtain an aimed compound.

Yield: 9.8 g (98%), Melting point: 240°–245° C.

EXAMPLE 6

Preparation of calcium 3-(4,6-dimethoxypyrimidin-2-yl)oxy-6-dimethylaminopicolinate (Compound No. 49)

1.0 g (3.1 mmol) of potassium 3-(4,6-dimethoxypyrimidin-2-yl)oxy-6-dimethylaminopicolinate was dissolved in 10 ml of tetrahydrofuran, and 0.15 g (1.5 mmol) of precipitated calcium carbonate was added thereto. Furthermore, 10 ml of water was added to the resultant mixture, and the mixture was stirred at room temperature. The reaction liquor was concentrated under reduced pressure, and acetone was added thereto to precipitate a crystal. The crystal thus obtained was separated by filtration and was washed with hexane to obtain an aimed compound.

Yield: 1.0 g (91%), Melting point: 169°–182° C.

EXAMPLE 7

Preparation of methoxymethyl 3-4,6-dimethoxypyrimidin-2-yl)oxy-6-dimethylaminopicolinate (Compound No. 41)

0.4 g (1.25 mmol) of 3-(4,6-dimethoxypyrimidin-2-yl)oxy-6-dimethylaminopicolinic acid was dissolved in 15 ml of dichloromethane, and 0.17 g (1.31 mmol) of diisopropylethylamine was added thereto under cooling to react for 15 minutes. Thereafter, 0.12 g (1.49 mmol) of methoxymethyl chloride was dropwise added thereto at 0° C., and the resultant mixture was reacted for 4 hours by gradually returning the temperature to room temperature. After the reaction, 30 ml of dichloromethane was further added thereto, and the reaction content was washed with water. Thereafter, the reaction content was washed with 10% citric acid aqueous solution and saturated salt water, and was dried, concentrated, and then purified with silica gel column chromatography to obtain an aimed compound.

Yeild: 0.4 g (84%), Melting point: 91°–96° C.

The starting compound for the compound of the present invention can be prepared in the following manner.

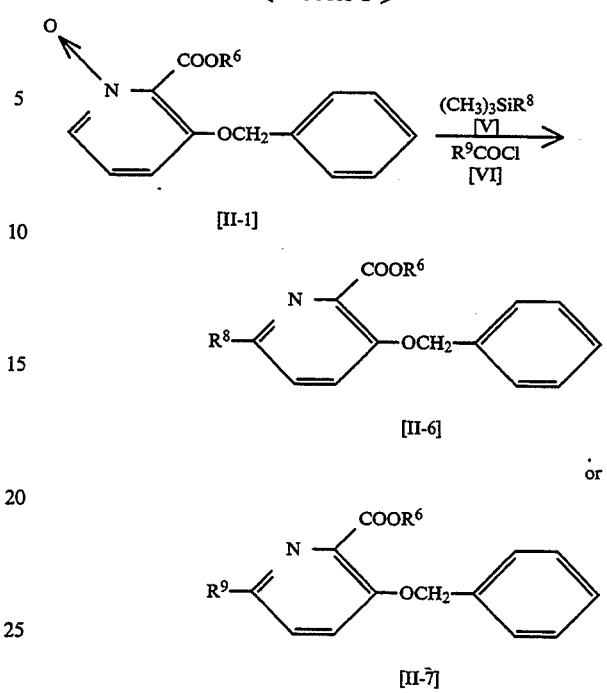

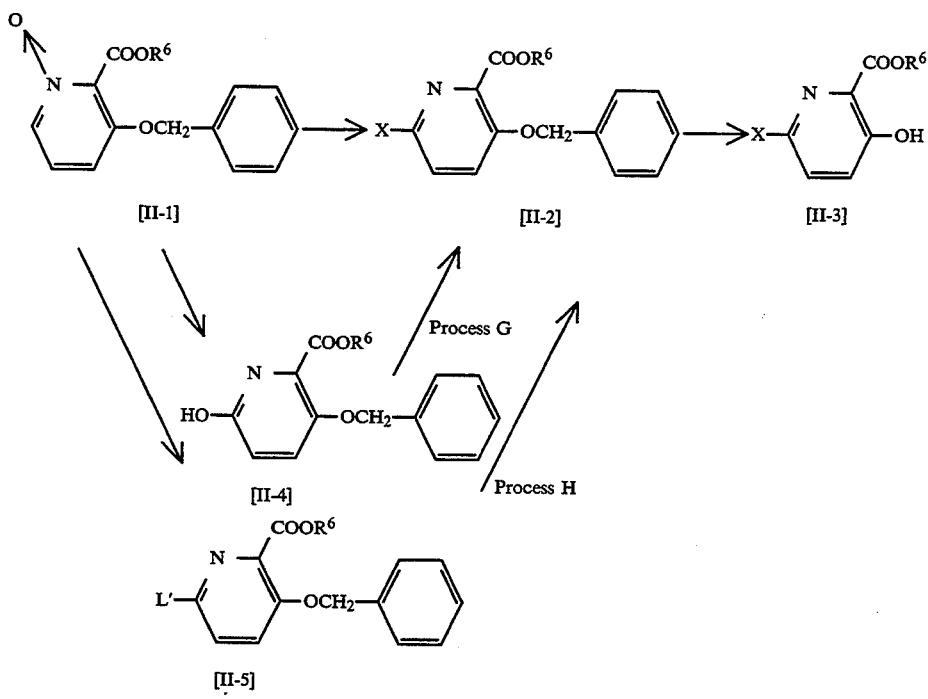

(wherein $R^6$ $L^1$ and X are as defined above.)

Thus, the compound of the formula II-3 can be prepared by converting the compound of the formula II-1 into the compound of the formula II-2 and then catalytically hydrogenating with hydrogen. The conversion of the compound of the formula II-1 respectively into the compound of the formula II-4 and the compound of the formula II-5 can be made by the known methods (see for example, Pharmacological Journal, Vol. 67, p. 51 (1947)). These methods are explained hereinafter in more detail.

(wherein $R^6$ is as defined above; $R^8$ is a cyano group, a dimethylamino group or a diethylamino group; and $R^9$ is a dimethylamino group, a diethylamino group, an alkyl group or a phenyl group.)

Thus, the compound of the formula II-6 or the compound of the formula II-7 can be prepared by reacting the compound of the formula II-1 with the trimethylsilyl derivative of the formula V or the acid chloride of the formula VI in an inert solvent within a temperature range of from room temperature to the boiling point of the solvent for several hours.

Examples of the solvent used herein include a hydrocarbon solvent such as benzene or toluene, a halogenated hydrocarbon solvent such as dichloromethane or chloroform, an ether solvent such as tetrahydrofuran or 1,4-dioxane, a ketone solvent such as acetone or methyl ethyl ketone, an ester solvent such as methyl acetate or ethyl acetate, an aprotic polar solvent such as dimethylformamide or dimethylacetamide, acetonitrile or others. Among them, chloroform is preferable.

<Process G>

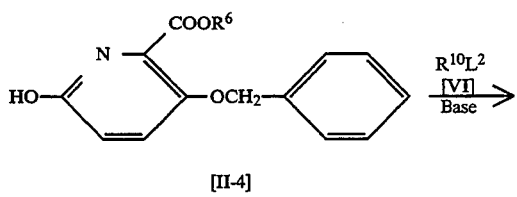

[II-4]

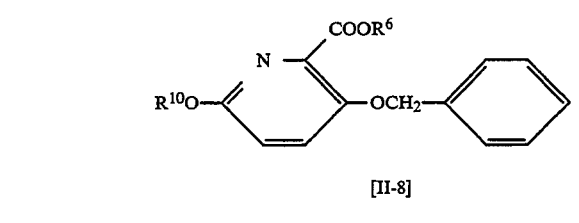

[II-8]

(wherein $R^6$ is as defined above; $R^{10}$ is an alkyl group, a substituted alkyl group or a 4,6-dimethoxypyrimidin-2-yl group; and $L^2$ is a halogen atom, provided that $L^2$ is a halogen atom or an alkylsulfonyl group when $R^{10°}$ is a 4,6-dimethoxypyrimidin-2-yl group.)

Thus, the compound of the formula II-8 can be prepared by reacting the compound of the formula II-4 with the compound of the formula VI in the presence of a base in an inert solvent within a temperature range of from room temperature to the boiling point of the solvent for from a few minutes to a few hours.

Examples of the solvent used herein include a hydrocarbon solvent such as benzene or toluene, a halogenated hydrocarbon solvent such as dichloromethane or chloroform, an ether solvent such as tetrahydrofuran or 1,4-dioxane, a ketone solvent such as acetone or methyl ethyl ketone, an ester solvent such as methyl acetate or ethyl acetate, an aprotic polar solvent such as dimethylformamide or dimethylacetamide, acetonitrile or others. Examples of the base used herein include alkali metals such as metal sodium or metal potassium, alkali metal hydrides and alkali earth metal hydrides such as sodium hydride, potassium hydride or calcium hydride, carbonates such as sodium carbonate, potassium carbonate or calcium carbonate, and metal hydroxides such as sodium hydroxide, potassium hydroxide or calcium hydroxide.

<Process H>

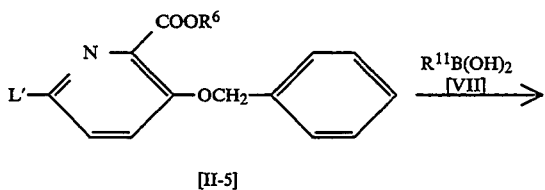

[II-5]

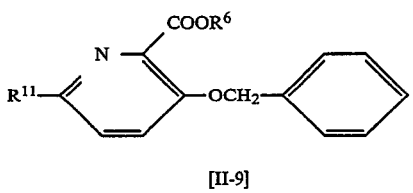

[II-9]

(wherein $R^6$ and $L^1$ are as defined above, and $R^{11}$ is a substituted phenyl group.)

Thus, the compound of the formula II-9 can be prepared by reacting the compound of the formula II-5 with the compound of the formula VII in the presence of a base and a catalyst in an inert solvent within a temperature range of from room temperature to the boiling point of the solvent for several hours.

Examples of the solvent used herein include a hydrocarbon solvent such as benzene or toluene, an alcohol solvent such as methanol or ethanol, an ether solvent such as 1,2-dimethoxyethane, tetrahydrofuran or ethyl ether, an ester solvent such as methyl acetate or ethyl acetate, an aprotic polar solvent such as dimethylformamide or dimethylacetamide, acetonitrile or others. Examples of the catalyst used include tetrakis (triphenylphosphine)palladium(O), triphenylphosphine-palladium acetate, and tris(O-tolyl)phosphine-palladium acetate. Examples of the base used include a carbonate such as sodium carbonate or potassium carbonate, a bicarbonate such as sodium hydrogen carbonate, or an organic base such as triethylamine or pyridine.

Furthermore, the starting compound can be prepared by the following process.

<Process I>

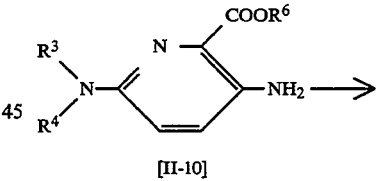

[II-10]

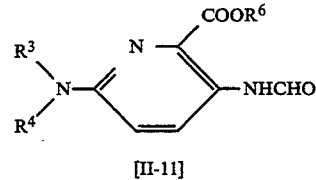

[II-11]

(wherein $R^3R^4$ and $R^6$ are as defined above.)

Thus, the compound of the formula II-11 can be prepared by reacting the compound of the formula II-10 with formic acid within a temperature range of from room temperature to the boiling point for from a few minutes to a few hours.

The compound of the formula II-11 can also be prepared by reacting the compound of the formula II-10 with a mixture of acetic anhydride-formic acid or dicyclohexylcarbodiimide formate.

<Process J>

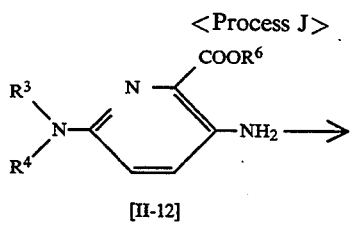

(wherein $R^3$, $R^4$ and $R^6$ are as defined above.)

Thus, the compound of the formula II-13 can be prepared by reacting the compound of the formula II-12 with sodium nitrite in the presence of a mineral acid at about 0° C. to obtain a diazonium salt and then treating the diazonium salt with sulfur or a sulfur compound.

Examples of the sulfur compound include an inorganic compound such as sodium sulfide or sodium hydrosulfide, and an organic compound such as benzylmercaptan or O-ethyl potassium dithiocarbonate. However, the production is not limited to these methods.

The production of the starting compound is described in further detail with reference to the following Reference Examples.

REFERENCE EXAMPLE 1

Preparation of methyl 3-benzyloxy-6-(N,N-dimethylamino)picolinate 15 g (58 mmol) of methyl 3-benzyloxypicolinate-N-oxide, 6.7 g (67 mmol) of trimethylsilylnitrile and 8.3 g (61 mmol) of N,N-dimethylcarbamoyl chloride were added to 100 ml of dichloromethane, and the mixture was allowed to stand at room temperature while stirring. The organic layer obtained was washed with water, dried and concentrated, and the residue thus obtained was purified by column chromatography to obtain an aimed compound.

Yield: 2.4 g (14%), Melting point: 71.5°-73° C.

REFERENCE EXAMPLE 2

In the same manner as above, methyl 3-benzyloxy-6-cyanopicolinate was obtained.

Yield: 3.1 g (20%), Melting point: 103.5°-105° C.

REFERENCE EXAMPLE 3

Preparation of methyl 3-benzyloxy-6-ethoxypicolinate 5.0 g (19 mmol) of methyl 3-benzyloxy-6-hydroxypicolinate, 2.1 g (19 mmol) of ethyl bromide and 2.9 g (21 mmol) of potassium carbonate were added to 100 ml of DMF, and the resultant mixture was reacted at 80° C. for 5 hours. After the reaction, the reaction content was poured into water, and was extracted with ethyl acetate, washed with water, dried and concentrated. The residue thus obtained was purified by column chromatography to obtain an aimed compound.

Yield: 4.1 g (74%), Melting point: 45°-46° C.

REFERENCE EXAMPLE 4

Preparation of methyl 3-benzyloxy-6-phenylpicolinate 0.6 g (0.5 mmol) of tetrakis(triphenylphosphine)palladium(O) and 5 ml of 1,2-dimethoxyethane were charged in a 100 ml three-forked flask equipped with a thermometer, a cooling tube and a nitrogen-introducing tube. Thereafter, 2.7 g (10.0 mmol) of methyl 3-benzyloxy-6-chloropicolinate was dissolved in 1,2-dimethoxyethane (20 ml) under nitrogen stream, and was added to the flask at one time. After stirring the resultant mixture at room temperature for 3 hours, 1.8 g (15.0 mmol) of phenylboric acid was dissolved in 1,2-dimethoxyethane (15 ml) and was added to the reaction mixture, which was further stirred for 1 hour. Thereafter, 2M-sodium carbonate aqueous solution (40 ml) was added to the reaction mixture, and the resultant mixture was heat-refluxed for 50 minutes. After cooling, an appropriate amount of water was added to the reaction mixture, and the mixture was extracted with ethyl acetate. The organic layer thus obtained was washed with water and saturated salt water, dried and concentrated, and the residue thus obtained was purified by column chromatography to obtain an aimed compound.

Yield: 1.9 g (59.4%)

REFERENCE EXAMPLE 5

Preparation of methyl 3-hydroxy-6-phenylpicolinate 1.9 g of methyl 3-benzyloxy-6-phenylpicolinate was reduced with 10% palladium carbon/methanol, and the resultant product was purified by column chromatography to obtain an aimed compound.

Yield: 1.0 g (76.9%), Melting point: 100°-101° C.

REFERENCE EXAMPLE 6

Preparation of methyl 6-(N,N-dimethylamino)-3-hydroxypicolinate 2.3 g (8 mmol) of methyl 3-benzyloxy-6-(N,N-dimethylamino)picolinate and 0.3 g of 10% palladium carbon were added to 100 ml of ethyl acetate, and was hydrogenated under normal pressure, after the reaction, the reaction product was filtrated and concentrated to obtain a crystal.

Yield: 1.4 g (92%), Melting point: 118.5°-120° C.

Concrete examples of the starting compounds prepared in the same manner as in Reference Examples 1 to 6 are enumerated in Table 2.

TABLE 2

| Intermediate compound No. | X | $R^{12}$ | Melting Point (°C.) |
|---|---|---|---|
| 1 | N(CH$_3$)$_2$ | CH$_2$—C$_6$H$_5$ | 71–73 |
| 2 | N(CH$_3$)$_2$ | H | 118.5–120 |

TABLE 2-continued

Structure: pyridine with COOCH3, N, X substituent, and $OR^{12}$ substituent

| Intermediate compound No. | X | $R^{12}$ | Melting Point (°C.) |
|---|---|---|---|
| 3 | CN | $CH_2$–phenyl | 103.5–105 |
| 4 | CN | H | |
| 5 | phenyl | $CH_2$–phenyl | |
| 6 | phenyl | H | 100–101 |
| 7 | $OCH_3$ | H | |
| 8 | $OC_2H_5$ | $CH_2$–phenyl | 45–46 |
| 9 | $OC_2H_5$ | H | |
| 10 | 4-$CH_3$–phenyl | $CH_2$–phenyl | 140–143 |
| 11 | 4-$CH_3$–phenyl | H | 84.5–86 |
| 12 | 4-Cl–phenyl | $CH_2$–phenyl | 127–130 |
| 13 | 4-Cl–phenyl | H | 142–145 |
| 14 | 4-F–phenyl | H | 124.5–127 |
| 15 | 4-$OCH_3$–phenyl | H | 82–85 |

The herbicidal composition of the present invention comprises the picolinic acid derivative having the formula (I) as an effective ingredient.

When the compound of the present invention is used as a herbicide in rice fields, upland fields, orchards and non-agricultural lands, the active ingredient may be used in an appropriate formulation depending on its use. In general, the active ingredient may be used in various formulations such as a dust, a wettable powder, an emulsifiable concentrate and a granule by diluting with an inert liquid or a solid carrier or optionally by blending with a surfactant, a dispersing agent or an adjuvant.

For example, the dust is prepared by blending and pulverizing the active ingredient with a solid carrier. The wettable powder can be prepared by blending and pulverizing the active ingredient with a solid carrier, a surfactant and a dispersing agent. The emulsifiable concentrate can be prepared by mixing the active ingredient with a liquid carrier, a surfactant and a dispersing agent. The granule can be prepared by blending and granulating the active ingredient with a solid carrier, a surfactant, a dispersing agent and an adjuvant, or by coating the active ingredient on a granule obtained by blending and granulating a solid carrier, a surfactant, a dispersing agent and an adjuvant.

As a carrier to be used for these formulations, there may be enumerated a solid carrier such as talc, bentonite, clay, kaolin, diatomaceous earth, white carbon, vermiculite, slaked lime, silica sand, ammonium sulfate or urea, or a liquid carrier such as isopropanol, xylene, cyclohexanone, isophorone or methyl naphthalene. As a surfactant and a dispersing agent, there may be enumerated, for example, an alcohol-sulfuric acid ester salt, an alkylaryl sulfonate, naphthalene sulfonate-formalin condensate, lignin sulfonate, a polyoxyethylene glycol ether, a polyoxyethylene alkyl aryl ether or a polyoxyethylene sorbitol monoalkylate. As an adjuvant, for example, carboxymethyl cellulose, polyethylene glycol or gum arabic may be enumerated.

The proportion of the active ingredient is optionally selected depending on its use, and it is usually from 0.01 to 10% by weight, preferably from 0.05 to 5% by weight, in the cases of dust and granule formulations, and from 1 to 50% by weight, preferably from 5 to 20% by weight, in the cases of emulsifiable concentrate and wettable powder formulations, but it is not limited thereto.

In practical use, the herbicide of the present invention may be diluted to a suitable concentration before applying to foliage, soil or water surface, or may be directly applied. The herbicide of the present invention is applied in a dose of from 0.1 g to 5 kg, preferably from 1 g to 1 kg of the active ingredient per 10 ares. In the case of liquid application such as emulsifiable concentrate and wettable powder formulations, the active ingredient is diluted to a concentration of from 0.1 to 50,000 ppm, preferably from 10 to 10,000 ppm for application, but it is not limited thereto.

If desired, the compound of the present invention may be used in combination with insecticides, sterilizers, other herbicides, plant growth controlling agents, fertilizers or the like.

Now, typical Formulation Examples for the herbicidal composition of the present invention will be given. In these Examples, "part" means "part by weight".

FORMULATION EXAMPLE 1 (dust).

1 Part of Compound No. 20 and 99 parts of diatomaceous earth were uniformly mixed and pulverized to obtain a dust.

FORMULATION EXAMPLE 2 (wettable powder)

10 Parts of Compound No. 19, 0.5 part of polyoxyethylenealkylaryl ether, 0.5 part of sodium naphthalenesulfonate-formalin condensate, 20 parts of diatomaceous earth and 69 parts of clay were uniformly mixed and pulverized to obtain a wettable powder.

FORMULATION EXAMPLE 3 (wettable powder)

10 Parts of Compound No. 1, 0.5 part of polyoxyethylenealkylaryl ether, 0.5 part of sodium naphthalenesulfonate-formalin condensate, 20 parts of diatomaceous earth, 5 parts of Carplex 80 and 64 parts of clay were uniformly mixed and pulverized to obtain a wettable powder.

FORMULATION EXAMPLE 4 (emulsifiable concentrate)

30 Parts of Compound No. 20, 60 parts of equivalent amount mixture of xylene and isophorone, and 10 parts of polyoxyethylenealkylaryl ether polymer and a metal salt of alkylbenzenesulfonic acid were uniformly mixed and stirred to obtain an emulsifiable concentrate.

FORMULATION EXAMPLE 5 (granule)

10 Parts of Compound No. 3, 80 parts of a bulking agent comprising a 1:3 mixture of talc and bentonite, 5 parts of white carbon, 5 parts of polyoxyethylenealkylaryl ether polymer and a metal salt of alkylbenzenesulfonic acid and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

EFFECT OF THE INVENTION

The compound having the general formula I of the present invention is effective for killing various troublesome weeds grown in upland field at a small dosage, examples of the weeds including broadleaf weeds such as morningglory (Ipomea sp.), common cocklebur (*Xanthum strumarium*), pale smartweed (*Polygonum lapathifolium*), slender amaranth (*Amaranthus viridis*), common lambsquarters (*Chenopodium album*), chickweed (*Stellaria media*), velveltleaf (*Abutilon theophrasti*) and prickly sida (*Sida spinosa*), perennial and annual cyperaceous weeds such as purple nutsedge (*Cyperus rotundus*), yellow nutsedge, *Kyllinga brevifolia*, umbrella plant (*Cyperus microiria*) and rice flatsedge (*Cyperus iria*), and gramineous weeds such as quackgrass (*Agropyron repens*), johnsongrass (*Sorghum halepense*), barnyardgrass (*Echinochloa crusgalli*), crabgrass (Digitaria sp.), foxtail (Setaria sp.), green foxtail (*Setaria viridis*) and goosegrass (*Eleusine indica*).

The compound of the present invention is also effective as a herbicide for troublesome weeds grown in non-agricultural land, such as Italian ryegrass (*Lolium multiflorum*), eulalia (*Miscanthus sinensis*), cogongrass (*Imperata cylindrica*), dayflower (*Commelina communis*), purslane (*Portulaca oleracea*), arrowroot (*Pueraria lobata*), tall goldenrod (*Solidago altissima*) and devils beggarticks (*Bidens frondasa*).

The compound of the present invention achieves excellent herbicidal effects at a very small dosage on annual weeds such as barnyardgrass (*Echinochloa crusgalli*), small flower flatsedge (*Cyperus difformis*) and monochoria (*Monochoria vaginalis*), and perennial weeds such as *Sagittaria pygmaea, Cyperus serotinus, Eleocharis kuroguwai*, bulrush (*Scirpus hotarui*) and *Alisma canaliculatum*, grown in paddy fields in a wide range from germinating stage to growing stage.

Now, the herbicidal effects of the compounds of the present invention will be described with reference to the following Test Examples.

In the Test Examples, the following compounds were used as Comparative Examples.

Compound A: ethyl
3-(4,6-dimethoxypyrimidin-2-yl)oxypicolinate
(Compound disclosed in Japanese Unexamined Patent Publication No. 84/1989)

Compound B: methyl
3-(4,6-dimethoxypyrimidin-2-yl)thiopicolinate
(Compound disclosed in Japanese Unexamined Patent Publication No. 121973/1990)

TEST EXAMPLE 1

(Herbicidal effect test by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 2 was diluted with water, and was applied dropwise to the water surface in such manner as to apply 100 g of the active ingredient per 10 ares,. The plants were then cultured in a green house, and the evaluation of the herbicidal effect was conducted on the 21st day after the treatment in accordance with the standards as identified in Table 3. The results are shown in the following Table 4.

TABLE 3

| Index No. | Herbicidal effects (grow-controlling degree) |
|---|---|
| 5 | Herbicidal effect: at least 90% |
| 4 | Herbicidal effect: at least 70% and less than 90% |
| 3 | Herbicidal effect: at least 50% and less than 70% |
| 2 | Herbicidal effect: at least 30% and less than 50% |
| 1 | Herbicidal effect: at least 10% and less than 30% |
| 0 | Herbicidal effect: 0 to less than 10% |

TABLE 4

| Compound No. | Herbicidal effects | | |
|---|---|---|---|
| | Ec | Mo | Sc |
| 1 | 5 | 5 | 5 |
| 2 | 5 | 5 | 5 |
| 3 | 5 | 5 | 5 |
| 4 | 5 | 5 | 5 |
| 19 | 5 | 5 | 5 |
| 20 | 5 | 5 | 5 |
| 21 | 5 | 5 | 4 |
| 22 | 5 | 5 | 4 |
| 23 | 5 | 5 | 5 |
| 24 | 5 | 5 | 5 |
| 27 | 5 | 5 | 5 |
| 35 | 5 | 5 | 5 |
| 36 | 5 | 5 | 5 |
| 37 | 5 | 5 | 5 |
| 38 | 5 | 5 | 5 |
| 39 | 5 | 5 | 5 |
| 40 | 5 | 5 | 5 |

TABLE 4-continued

| Compound No. | Herbicidal effects | | |
|---|---|---|---|
| | Ec | Mo | Sc |
| 41 | 5 | 5 | 5 |
| 42 | 5 | 5 | 5 |
| 43 | 5 | 5 | 5 |
| 44 | 5 | 5 | 5 |
| 45 | 5 | 5 | 5 |
| 46 | 5 | 5 | 5 |
| 47 | 5 | 5 | 5 |
| 48 | 5 | 5 | 5 |
| 49 | 5 | 5 | 5 |
| 56 | 5 | 5 | 5 |
| 57 | 5 | 5 | 5 |
| 63 | 5 | 5 | 5 |

TEXT EXAMPLE 2

(Herbicidal effect test by upland field soil treatment)

In a plastic pot (surface area: 100 cm$^2$) filled with paddy field soil, barnyardgrass (Ec), pale smartweed (Po), slender amaranth (Am), common lambsquarters (Ch) and rice flatsedge (Ci) were sown and covered with soil. A wettable powder prepared in accordance with Formulation Example 2 was diluted with water, and applied uniformly to the soil surface by a small-sized sprayer in an amount of 100 1/10 ares so as to apply 100 g of the active ingredient per 10 ares. The plants were then cultured in a green house, and the evaluation of the herbicidal effect was conducted on the 20th day after the treatment in accordance with the standard as identified in the above Table 3. The results are shown in the following Table 5.

TABLE 5

| Compound No. | Herbicidal effects | | | | |
|---|---|---|---|---|---|
| | Ec | Po | Am | Ch | Ci |
| 1 | 5 | 5 | 5 | 5 | 5 |
| 2 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 22 | 5 | 5 | 5 | 5 | 5 |
| 24 | 5 | 5 | 5 | 5 | 5 |
| 25 | 4 | 5 | 5 | 5 | 4 |
| 27 | 5 | 5 | 5 | 5 | 5 |
| 35 | 5 | 4 | 5 | 5 | 5 |
| 36 | 5 | 5 | 4 | 5 | 5 |
| 37 | 4 | 4 | 4 | 5 | 5 |
| 38 | 5 | 5 | 5 | 5 | 5 |
| 39 | 5 | 5 | 5 | 5 | 5 |
| 40 | 5 | 5 | 5 | 5 | 5 |
| 41 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 45 | 5 | 5 | 5 | 5 | 5 |
| 46 | 5 | 5 | 5 | 5 | 5 |
| 48 | 5 | 5 | 5 | 5 | 5 |
| 49 | 5 | 5 | 5 | 5 | 5 |
| 56 | 5 | 5 | 5 | 5 | 5 |
| 57 | 5 | 5 | 5 | 5 | 5 |
| 63 | 5 | 5 | 5 | 5 | 5 |

TEXT EXAMPLE 3

(Herbicidal effect test by upland field foliage treatment)

In a plastic pot (surface area: 100 cm$^2$) filled with upland field soil, barnyardgrass (Ec), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 2 was diluted with water, and applied onto the total foliages of the plant from upward by a small-sized sprayer in an amount of 100 1/10 ares so as to apply 100 g of the active ingredient per 10 ares. The plants were then cultured in the green house, and the evaluation of the herbicidal effect was conducted on the 14th day after the treatment in accordance with the standard as identified in the above Table 3. The results are shown in the following Table 6.

TABLE 6

| Compound No. | Herbicidal effects | | | | |
|---|---|---|---|---|---|
| | Ec | Po | Am | Ch | Ci |
| 1 | 5 | 5 | 5 | 5 | 5 |
| 2 | 5 | 5 | 5 | 5 | 5 |
| 19 | 5 | 5 | 5 | 5 | 5 |
| 20 | 5 | 5 | 5 | 5 | 5 |
| 21 | 5 | 4 | 5 | 5 | 5 |
| 22 | 5 | 4 | 4 | 5 | 5 |
| 23 | 4 | 5 | 4 | 5 | 5 |
| 24 | 5 | 5 | 5 | 5 | 5 |
| 27 | 5 | 5 | 5 | 5 | 5 |
| 35 | 5 | 5 | 5 | 5 | 5 |
| 36 | 5 | 5 | 5 | 5 | 5 |
| 37 | 5 | 5 | 5 | 5 | 5 |
| 38 | 5 | 5 | 5 | 5 | 5 |
| 39 | 5 | 5 | 5 | 5 | 5 |
| 40 | 5 | 5 | 5 | 5 | 5 |
| 41 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 45 | 5 | 5 | 5 | 5 | 5 |
| 46 | 5 | 5 | 5 | 5 | 5 |
| 48 | 5 | 5 | 5 | 5 | 5 |
| 49 | 5 | 5 | 5 | 5 | 5 |
| 56 | 5 | 5 | 4 | 5 | 5 |
| 57 | 5 | 5 | 5 | 4 | 5 |
| 63 | 5 | 5 | 5 | 5 | 5 |

TEXT EXAMPLE 4

(Herbicidal effect test by upland field foliage treatment at a small dosage)

In a plastic pot (surface area: 600 cm$^2$) filled with upland field soil, barnyardgrass (Ec), johnsongrass (So), pale smartweed (Po), slender amaranth (Am), common lambsquarters (Ch), morningglory (Ip) and common cocklebur (Xa) were sown and covered with soil, and were cultured in a green house for 2 weeks. A predetermined amount of a wettable powder prepared in accordance with Formulation Example 2 was diluted with water, and applied onto the total foliages of the plant from upward by a small-sized sprayer in an amount of 100 1/10 ares. The plants were then cultured in the green house, and the evaluation of the herbicidal effect was conducted on the 14th day after the treatment in accordance with the standard as identified in the above Table 3. The results are shown in the following Table 7.

TABLE 7

| Compound No. | Dose of active ingredient (g/10a) | Herbicidal effects | | | | | | |
|---|---|---|---|---|---|---|---|---|
| | | Ec | So | Po | Am | Ch | Ip | Xa |
| 19 | 6.3 | 5 | 5 | 5 | 5 | 5 | 5 | 5 |
| 20 | 6.3 | 5 | 5 | 5 | 5 | 5 | 5 | 5 |
| 38 | 6.3 | 5 | 5 | 5 | 5 | 5 | 5 | 5 |
| 39 | 6.3 | 5 | 5 | 5 | 5 | 5 | 5 | 5 |
| 40 | 6.3 | 5 | 5 | 5 | 5 | 5 | 5 | 5 |
| 41 | 6.3 | 5 | 5 | 5 | 5 | 5 | 5 | 5 |
| 42 | 6.3 | 5 | 5 | 5 | 5 | 5 | 5 | 5 |
| 44 | 6.3 | 5 | 5 | 5 | 5 | 5 | 5 | 5 |
| 45 | 6.3 | 5 | 5 | 5 | 5 | 5 | 5 | 5 |

TABLE 7-continued

| Compound No. | Dose of active ingredient (g/10a) | Herbicidal effects | | | | | | |
|---|---|---|---|---|---|---|---|---|
| | | Ec | So | Po | Am | Ch | Ip | Xa |
| 47 | 6.3 | 5 | 5 | 5 | 5 | 5 | 5 | 5 |
| 48 | 6.3 | 5 | 5 | 5 | 5 | 5 | 5 | 5 |
| 49 | 6.3 | 5 | 5 | 5 | 5 | 5 | 5 | 5 |
| 57 | 6.3 | 5 | 5 | 5 | 5 | 5 | 5 | 5 |
| 63 | 6.3 | 5 | 5 | 5 | 5 | 5 | 5 | 5 |
| A | 6.3 | 1 | 4 | 4 | 5 | 4 | 1 | 1 |
| B | 6.3 | 0 | 2 | 3 | 1 | 3 | 0 | 0 |

TEST EXAMPLE 5

(Herbicidal effect test by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 2 was diluted with water, and was applied dropwise to the water surface in such manner as to apply 100 g of the active ingredient per 10 ares,. The plants were then cultured in a green house, and the evaluation of the herbicidal effect was conducted on the 21st day after the treatment in accordance with the standards as identified in Table 3. The results are shown in the following Table 8.

TABLE 8

| Compound No. | Herbicidal effects | | |
|---|---|---|---|
| | Ec | Mo | Sc |
| 66 | 5 | 5 | 5 |
| 67 | 5 | 5 | 5 |
| 75 | 5 | 5 | 5 |
| 76 | 5 | 5 | 5 |
| 77 | 5 | 5 | 5 |
| 78 | 5 | 5 | 5 |
| 79 | 5 | 5 | 5 |
| 80 | 5 | 5 | 5 |
| 81 | 5 | 5 | 5 |
| 83 | 5 | 5 | 5 |
| 86 | 5 | 5 | 5 |
| 87 | 5 | 5 | 5 |
| 88 | 5 | 5 | 5 |
| 89 | 5 | 5 | 5 |
| 90 | 5 | 5 | 5 |
| 92 | 5 | 5 | 5 |
| 93 | 5 | 5 | 5 |
| 95 | 5 | 5 | 5 |
| 96 | 5 | 5 | 5 |
| 97 | 5 | 5 | 5 |
| 98 | 5 | 5 | 5 |
| 101 | 5 | 5 | 5 |
| 103 | 5 | 5 | 5 |
| 104 | 5 | 5 | 5 |
| 105 | 5 | 5 | 5 |
| 106 | 5 | 5 | 5 |

TEST EXAMPLE 6

(Herbicidal effect test by upland field soil treatment)

In a plastic pot (surface area: 100 cm$^2$) filled with paddy field soil, barnyardgrass (Ec), pale smartweed (Po), slender amaranth (Am), common lambsquarters (Ch) and rice flatsedge (Ci) were sown and covered with soil. A wettable powder prepared in accordance with Formulation Example 2 was diluted with water, and applied uniformly to the soil surface by a small-sized sprayer in an amount of 100 l/10 ares so as to apply 100 g of the active ingredient per 10 ares. The plants were then cultured in a green house, and the evaluation of the herbicidal effect was conducted on the 20th day after the treatment in accordance with the standard as identified in the above Table 3. The results are shown in the following Table 9.

TABLE 9

| Compound No. | Herbicidal effects | | | | |
|---|---|---|---|---|---|
| | Ec | Po | Am | Ch | Ci |
| 66 | 5 | 5 | 5 | 5 | 5 |
| 67 | 5 | 5 | 5 | 5 | 5 |
| 75 | 5 | 5 | 5 | 5 | 5 |
| 76 | 5 | 5 | 5 | 5 | 5 |
| 77 | 5 | 5 | 5 | 5 | 5 |
| 78 | 5 | 5 | 5 | 5 | 5 |
| 79 | 5 | 5 | 5 | 5 | 5 |
| 80 | 5 | 5 | 5 | 5 | 5 |
| 81 | 5 | 5 | 5 | 5 | 5 |
| 83 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 92 | 5 | 5 | 5 | 4 | 5 |
| 93 | 5 | 5 | 5 | 5 | 5 |
| 95 | 5 | 5 | 5 | 5 | 5 |
| 96 | 5 | 5 | 5 | 5 | 5 |
| 97 | 5 | 5 | 5 | 5 | 5 |
| 98 | 5 | 5 | 5 | 5 | 5 |
| 101 | 5 | 5 | 5 | 5 | 5 |
| 103 | 5 | 5 | 5 | 5 | 5 |
| 104 | 5 | 5 | 4 | 5 | 5 |
| 105 | 5 | 5 | 5 | 4 | 5 |
| 106 | 5 | 5 | 5 | 5 | 5 |

TEST EXAMPLE 7

(Herbicidal effect test by upland field foliage treatment)

In a plastic pot (surface area: 100 cm$^2$) filled with upland field soil, barnyardgrass (Ec), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 2 was diluted with water, and applied onto the total foliages of the plant from upward by a small-sized sprayer in an amount of 100 l/10 ares so as to apply 100 g of the active ingredient per 10 ares. The plants were then cultured in the green house, and the evaluation of the herbicidal effect was conducted on the 14th day after the treatment in accordance with the standard as identified in the above Table 3. The results are shown in the following Table 10.

TABLE 10

| Compound No. | Herbicidal effects | | | | |
|---|---|---|---|---|---|
| | Ec | Po | Am | Ch | Ci |
| 66 | 5 | 5 | 5 | 5 | 5 |
| 67 | 5 | 5 | 5 | 5 | 5 |
| 75 | 5 | 5 | 5 | 5 | 5 |
| 76 | 5 | 5 | 5 | 5 | 5 |
| 77 | 5 | 5 | 5 | 5 | 5 |
| 78 | 5 | 5 | 5 | 5 | 5 |
| 79 | 5 | 5 | 5 | 5 | 5 |
| 80 | 5 | 5 | 5 | 5 | 5 |
| 81 | 5 | 5 | 5 | 5 | 5 |
| 83 | 5 | 5 | 5 | 5 | 5 |
| 85 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 92 | 5 | 5 | 5 | 5 | 5 |
| 93 | 5 | 5 | 5 | 5 | 5 |
| 95 | 5 | 5 | 5 | 5 | 5 |

TABLE 10-continued

| Compound No. | Herbicidal effects | | | | |
|---|---|---|---|---|---|
| | Ec | Po | Am | Ch | Ci |
| 96 | 5 | 5 | 5 | 5 | 5 |
| 97 | 5 | 5 | 5 | 5 | 5 |
| 98 | 5 | 5 | 5 | 5 | 5 |
| 101 | 5 | 5 | 5 | 5 | 5 |
| 102 | 5 | 5 | 5 | 5 | 5 |
| 103 | 5 | 5 | 5 | 5 | 5 |
| 104 | 5 | 5 | 4 | 5 | 5 |
| 105 | 5 | 5 | 5 | 4 | 5 |
| 106 | 5 | 5 | 5 | 5 | 5 |
| 108 | 5 | 4 | 5 | 4 | 4 |

TEST EXAMPLE 8

(Herbicidal effect test by upland field foliage treatment at a small dosage)

In a plastic pot (surface area: 600 cm$^2$) filled with upland field soil, barnyardgrass (Ec), johnsongrass (So), pale smartweed (Po), slender amaranth (Am), common lambsquarters (Ch) were sown and covered with soil, and were cultured in a green house for 2 weeks. A predetermined amount of a wettable powder prepared in accordance with Formulation Example 2 was diluted with water, and applied onto the total foliages of the plant from upward by a small-sized sprayer in an amount of 100 l/10 ares. The plants were then cultured in the green house, and the evaluation of the herbicidal effect was conducted on the 14th day after the treatment in accordance with the standard as identified in the above Table 3. The results are shown in the following Table 11.

TABLE 11

| Compound No. | Dose of active ingredient (g/10a) | Herbicidal effects | | | | |
|---|---|---|---|---|---|---|
| | | Ec | So | Po | Am | Ch |
| 66 | 1.6 | 5 | 5 | 5 | 5 | 5 |
| 67 | 1.6 | 5 | 5 | 5 | 5 | 5 |
| 75 | 1.6 | 5 | 4 | 4 | 4 | 5 |
| 76 | 1.6 | 5 | 5 | 5 | 5 | 5 |
| 77 | 1.6 | 5 | 5 | 5 | 5 | 5 |
| 78 | 1.6 | 5 | 5 | 5 | 5 | 5 |
| 79 | 1.6 | 5 | 5 | 5 | 5 | 4 |
| 80 | 1.6 | 5 | 5 | 5 | 5 | 5 |
| 81 | 1.6 | 5 | 5 | 5 | 5 | 5 |
| 83 | 1.6 | 5 | 2 | 5 | 5 | 5 |
| 86 | 1.6 | 5 | 5 | 5 | 5 | 5 |
| 87 | 1.6 | 5 | 5 | 5 | 5 | 5 |
| 88 | 1.6 | 5 | 5 | 5 | 5 | 5 |
| 89 | 1.6 | 5 | 5 | 5 | 4 | 5 |
| 90 | 1.6 | 5 | 5 | 5 | 5 | 5 |
| 92 | 1.6 | 5 | 5 | 5 | 5 | 4 |
| 93 | 1.6 | 5 | 5 | 5 | 5 | 5 |
| 95 | 1.6 | 5 | 5 | 5 | 5 | 5 |
| 96 | 1.6 | 5 | 5 | 5 | 5 | 4 |
| 97 | 1.6 | 5 | 5 | 2 | 5 | 5 |
| 98 | 1.6 | 5 | 5 | 5 | 5 | 2 |
| 101 | 1.6 | 5 | 5 | 5 | 5 | 4 |
| 102 | 1.6 | 5 | 5 | 5 | 5 | 4 |
| 103 | 1.6 | 5 | 5 | 5 | 5 | 5 |
| 104 | 1.6 | 5 | 5 | 5 | 5 | 5 |
| 105 | 1.6 | 5 | 5 | 5 | 4 | 3 |
| 106 | 1.6 | 5 | 5 | 5 | 5 | 5 |

What is claimed is:

1. A picolinic acid derivative having the formula:

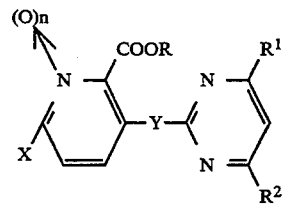

wherein R is a hydrogen atom, a ($C_1$-$C_4$) alkyl group, a ($C_2$-$C_4$) alkenyl group, a ($C_2$-$C_4$) alkynyl group, a benzyl group, a halogen-substituted ($C_1$-$C_4$) alkyl group, a cyano ($C_1$-$C_4$)alkyl group, a ($C_1$-$C_4$) alkoxy ($C_1$-$C_4$) alkyl group, a ($C_1$-$C_4$) alkoxycarbonyloxy ($C_1$-$C_4$) alkyl group, a ($C_1$-$C_4$) alkyl group, a cyclo ($C_4$-$C_7$) alkylcarbonyloxy ($C_1$-$C_4$) alkyl group, a cyclo ($C_3$-$C_6$) alkyl ($C_1$-$C_4$) alkyl group, an alkali metal atom selected from the group consisting of sodium and potassium, an alkali earth metal atom or an organic amine cation selected from the group consisting of a ($C_1$-$C_4$) alkylamino and a di-($C_1$-$C_4$) alkylamine; $R^1$ and $R^2$ are the same or different, and are a ($C_1$-$C_4$) alkyl group, a ($C_1$-$C_4$) alkoxy group, a halogen atom, a halogen-substituted ($C_1$-$C_4$) alkoxy group or a ($C_1$-$C_4$) alkylsulfonyl group; X is a group having the formula

wherein $R^3$ and $R^4$ are the same or different, and are a hydrogen atom, a ($C_1$-$C_4$) alkyl group, a phenyl group or a ($C_1$-$C_4$) acyl group; a cyano group; a phenyl group which may be substituted with a halogen atom, a ($C_1$-$C_4$) alkyl group or a ($C_1$-$C_4$) alkoxy group; a phenoxy group; a ($C_2$-$C_4$) alkenyl group; a ($C_2$-$C_4$) alkynyl group; a hydroxyl group; a trimethylsilylethynyl group; a nitro group; a 4,6-dimethoxypyrimidin-2-yloxy group; or a hydrogen atom; Y is an oxygen atom or a group having the formula

wherein $R^5$ is a hydrogen atom or a formyl group; and n is 0 or 1; provided that when X is a hydrogen atom, Y is a group having the formula

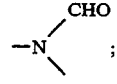

or a salt thereof.

2. A picolinic acid derivative having the formula:

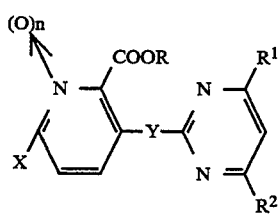

wherein R is a hydrogen atom, a (C₁–C₄) alkyl group, a alkenyl group, a (C₂–C₄) alkynyl group, a benzyl group, a halogen-substituted (C₁–C₄) alkyl group, a cyano(C₁–C₄)alkyl group, a (C₁–C₄) alkoxy (C₁–C₄) alkyl group, a (C₁–C₄) alkoxycarbonyloxy (C₁–C₄) alkyl group, a (C₁–C₄) alkoxycarbonyl (C₁–C₄) alkyl group, a (C₁–C₄) alkylcarbonyloxy (C₁–C₄) alkyl group, a cyclo (C₄–C₇) alkylcarbonyloxy (C₁–C₄) alkyl group, a cyclo (C₃–C₆) alkyl (C₁–C₄) alkyl group, an alkali metal atom selected from the group consisting of sodium and potassium, an alkali earth metal atom or an organic amine cation selected from the group consisting of a (C₁–C₄) alkylamine and a di-(C₁–C₄)alkylamine; R¹ and R² are the same or different, and are a (C₁–C₄) alkyl group, a (C₁–C₄) alkoxy group, a halogen atom, a halogen-substituted (C₁–C₄) alkoxy group or a (C₁–C₄) alkylsulfonyl group;

X is a cyano group or a group having the formula

wherein R³ and R⁴ are the same or different, and are a hydrogen atom, a (C₁–C₄) alkyl group, a phenyl group or a (C₁–C₄) acyl group;

Y is an oxygen atom or a group having the formula

wherein R⁵ is a hydrogen atom or a formyl group; and n is 0 or 1; or a salt thereof.

3. A picolinic acid derivative having the formula:

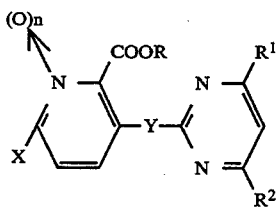

wherein R is a hydrogen atom, a (C₂–C₄) alkyl group, a (C₁–C₄) alkenyl group, a (C₂–C₄) alkynyl group, a benzyl group, a halogen-substituted (C₁–C₄) alkyl group, a (C₁–C₄) alkoxycarbonyloxy (C₁–C₄) alkyl group, a (C₁–C₄) alkoxycarbonyl (C₁–C₄) alkyl group, a (C₁–C₄) alkylcarbonyloxy (C₁–C₄) alkyl group, a cyclo (C₄–C₇) alkylcarbonyloxy (C₁–C₄) alkyl group, a cyclo (C₃–C₆) alkyl (C₁–C₄) alkyl group, an alkali metal atom selected from the group consisting of sodium and potassium, an alkali earth metal atom or an organic amine cation selected from the group consisting of a (C₁–C₄) alkylamine and a di-(C₁–C₄) alkylamine; R¹ and R² are the same or different, and are a (C₁–C₄) alkyl group, a (C₁–C₄) alkoxy group, a halogen atom, a halogen-substituted (C₁–C₄) alkoxy group or a (C₁–C₄) alkylsulfonyl group;

X is a phenyl group which may be substituted with a halogen atom, a (C₁–C₄) alkyl group or a (C₁–C₄) alkoxy group, or a phenoxy group;

Y is an oxygen atom or a group having the formula

wherein R⁵ is a hydrogen atom or a formyl group; and n is 0 or 1; or a salt thereof.

4. A picolinic acid derivative having the formula:

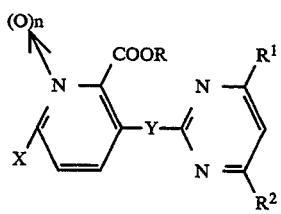

wherein R is a hydrogen atom, a (C₁–C₄) alkyl group, a (C₂–C₄) alkenyl group, a (C₂–C₄) alkynyl group, a benzyl group, a halogen-substituted (C₁–C₄) alkyl group, a cyano(C₁–C₄)alkyl group, a (C₁–C₄) alkoxy (C₁–C₄) alkyl group, a (C₁–C₄) alkoxycarbonyloxy (C₁–C₄) alkyl group, a (C₁–C₄) alkoxycarbonyl (C₁–C₄) alkyl group, a (C₁–C₄) alkylcarbonyloxy (C₁–C₄) alkyl group, a cyclo (C₄–C₇) alkylcarbonyloxy (C₁–C₄) alkyl group, a cyclo (C₃–C₆) alkyl (C₁–C₄) alkyl group, an alkali metal atom selected from the group consisting of sodium and potassium, calcium or an organic amine cation selected from the group consisting of a (C₁–C₄) alkylamine and a di-(C₁–C₄) alkylamine; R¹ and R² are the same or different, and are a (C₁–C₄) alkyl group, a (C₁–C₄) alkoxy group, a halogen atom, a halogen-substituted (C₁–C₄) alkoxy group or a (C₁–C₄) alkylsulfonyl group;

X is a (C₂–C₄) alkenyl group, a (C₂–C₄) alkynyl group, a hydroxyl group, a trimethylsilylethynyl group, a nitro group, a 4,6-dimethoxypyrimidin-2-yloxy group, or a hydrogen atom;

Y is an oxygen atom or a group having the formula

wherein R⁵ is a hydrogen atom or a formyl group; and n is 0 or 1;

provided that when X is a hydrogen atom, Y is a group having the formula

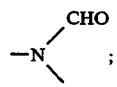 ;

or a salt thereof.

5. The picolinic acid derivative or the salt thereof according to claim 1, wherein R is a hydrogen atom or (C₁–C₄) alkyl group;

$R^1$ and $R^2$ are the same or different, and are a (C₁–C₄) alkyl group, a (C₁–C₄) alkoxy group, a halogen atom, a halogen-substituted (C₁–C₄) alkoxy group or a (C₁–C₄) alkylsulfonyl group;

X is a group having the formula

wherein $R^3$ and $R^4$ are the same or different, and are a hydrogen atom, a (C₁–C₄) alkyl group, a phenyl group or a (C₁–C₄) acyl group; a cyano group; a phenyl group which may be substituted with a halogen atom, a (C₁–C₄) alkyl group or a (C₁–C₄) alkoxy group; a phenoxy group; a hydroxyl group; a nitro group; or a 4,6-dimethoxypyrimidin-2-yloxy group;

Y is an oxygen atom or a group having the formula

wherein $R^5$ is a hydrogen atom or a formyl group, and n is 0 or 1.

6. The picolinic acid derivative or the salt thereof according to claim 1, wherein R is a hydrogen atom, a (C₁–C₄) alkyl group, a (C₂–C₄) alkenyl group, a (C₂–C₄) alkynyl group, a benzyl group, a halogen-substituted (C₁–C₄) alkyl group, a cyano (C₁–C₄) alkyl group, a (C₁–C₄) alkoxy (C₁–C₄) alkyl group, a (C₁–C₄) alkoxycarbonyloxy (C₁–C₄) alkyl group, a (C₁–C₄) alkoxycarbonyl (C₁–C₄) alkyl group, a (C₁–C₄) alkylcarbonyloxy (C₁–C₄) alkyl group, a cyclo (C₄–C₇) alkylcarbonyloxy (C₁–C₄) alkyl group, a cyclo (C₃–C₆) alkyl (C₁–C₄) alkyl group, an alkali metal atom selected from the group consisting of sodium and potassium, calcium, or an organic amine cation selected from the group consisting of a (C₁–C₄) alkylamine and a di-(C₁–C₄) alkylamine; $R^1$ and $R^2$ are the same or different, and are a (C₁–C₄) alkyl group, a (C₁–C₄) alkoxy group, a halogen atom, a halogen-substituted (C₁–C₄) alkoxy group or a (C₁–C₄) alkylsulfonyl group; X is a cyano group or a group having the formula

wherein $R^3$ and $R^4$ are the same or different, and are a hydrogen atom, a (C₁–C₄) alkyl group, a phenyl group or a (C₁–C₄) acyl group; Y is an oxygen atom, and n is 0; or a salt thereof.

7. The picolinic acid derivative or the salt thereof according to claim 1, wherein R is a hydrogen atom, a methyl group, an ethoxycarbonylmethyl group, a 1-propionyloxyethyl group, a 1-ethoxycarbonyloxyethyl group, a methoxymethyl group, a cyanomethyl group, a 2-chloroethyl group, a 2-propinyl group, an allyl group, a benzyl group, sodium or potassium;

$R^1$ and $R^2$ are a methoxy group;

X is a dimethylamino group or a vinyl group;

Y is an oxygen atom, and n is 0.

8. 3-(4,6-dimethoxypyrimidin-2-yl)oxy-6-(N,N-dimethylamino) picolinic acid.

9. Methoxymethyl 3-(4,6-dimethoxypyrimidin-2-yl)oxy-6-dimethylaminopyridine-2-carboxylate.

10. 3-(4,6-dimethoxypyrimidin-2-yl)oxy-6-(N-methylamino) picolinic acid.

11. A herbicidal composition comprising a herbicidally effective amount of a picolinic acid derivative or a salt thereof as defined in claim 1 and an agricultural adjuvant.

12. A herbicidal composition comprising a herbicidally effective amount of a picolinic acid derivative or a salt thereof as defined in claim 5 and an agricultural adjuvant.

13. A method for killing weeds which comprises applying a herbicidally effective amount of a picolinic acid derivative or a salt thereof as defined in claim 1 to a locus to be protected.

* * * * *